(12) United States Patent
Luo et al.

(10) Patent No.: US 8,821,745 B2
(45) Date of Patent: Sep. 2, 2014

(54) HIGH YIELD PREPARATION OF MACROSCOPIC GRAPHENE OXIDE MEMBRANES

(75) Inventors: Zhengtang Luo, Rocky Hill, CT (US); Alan T. Johnson, Philadelphia, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 442 days.

(21) Appl. No.: 13/141,402

(22) PCT Filed: Dec. 4, 2009

(86) PCT No.: PCT/US2009/066685
§ 371 (c)(1),
(2), (4) Date: Sep. 14, 2011

(87) PCT Pub. No.: WO2010/074918
PCT Pub. Date: Jul. 1, 2010

(65) Prior Publication Data
US 2012/0107593 A1    May 3, 2012

Related U.S. Application Data

(60) Provisional application No. 61/140,555, filed on Dec. 23, 2008.

(51) Int. Cl.
*B44C 1/22* (2006.01)
*G01N 27/414* (2006.01)
*C01B 31/04* (2006.01)

(52) U.S. Cl.
CPC ........... *C01B 31/043* (2013.01); *B01D 2325/26* (2013.01); *B01D 2323/34* (2013.01); *G01N 27/4145* (2013.01)

USPC .................................. 216/83; 216/13; 216/94

(58) Field of Classification Search
USPC ................................. 216/13, 83, 94
See application file for complete search history.

(56) References Cited

U.S. PATENT DOCUMENTS

| | | | |
|---|---|---|---|
| 2006/0241237 A1* | 10/2006 | Drzal et al. | 524/495 |
| 2007/0092432 A1 | 4/2007 | Prud'Homme et al. | |
| 2007/0131915 A1 | 6/2007 | Stankovich et al. | |
| 2008/0206124 A1 | 8/2008 | Jang et al. | |
| 2008/0258359 A1 | 10/2008 | Zhamu et al. | |
| 2009/0235721 A1* | 9/2009 | Robinson et al. | 73/31.05 |
| 2010/0126660 A1* | 5/2010 | O'Hara | 156/249 |
| 2010/0323178 A1* | 12/2010 | Ruoff et al. | 428/220 |

OTHER PUBLICATIONS

Gilje et al., "A Chemical Route to Graphene for Device Applications", Nano Letters, Oct. 2007, 7(11), 3394-3398.
Gomez-Navarro et al., "Electronic Transport Properties of Individual Chemically Reduced Graphene Oxide Sheets", Nano Letters, Oct. 2007, 7(11), 3499-3503.
Paredes et al., "Graphene Oxide Dispersions in Organic Solvents", Aug. 2008, 24(19), 10560-10564.

* cited by examiner

*Primary Examiner* — Shamim Ahmed
(74) *Attorney, Agent, or Firm* — Baker & Hostetler LLP

(57) ABSTRACT

Disclosed are graphene oxide membrane materials of high surface area, which membranes suitably have a surface area of above about 200 μm and exhibit electrical conductivity in excess of about 200 S/m. Also provided are methods of synthesizing such membranes, as well as devices and sensors that incorporate these novel grapheme materials.

12 Claims, 8 Drawing Sheets

Figure S1
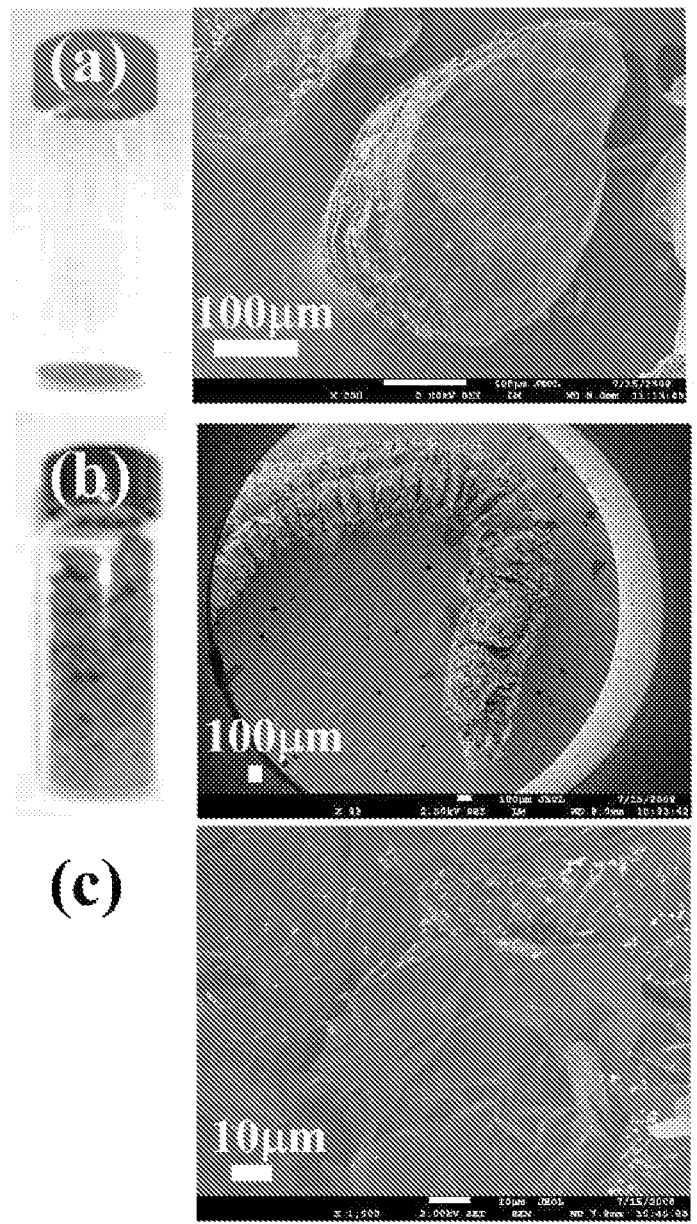

Figure S2
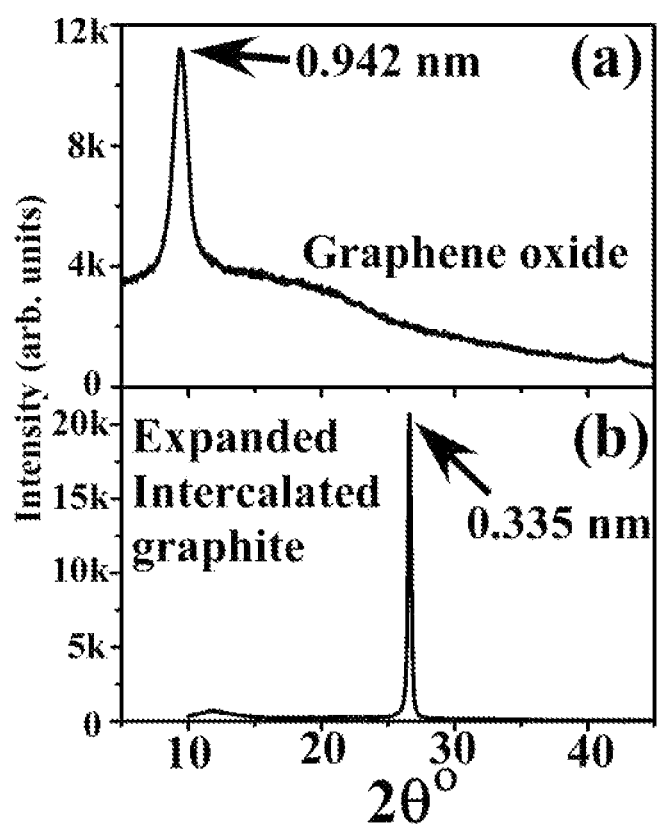

Figure S3
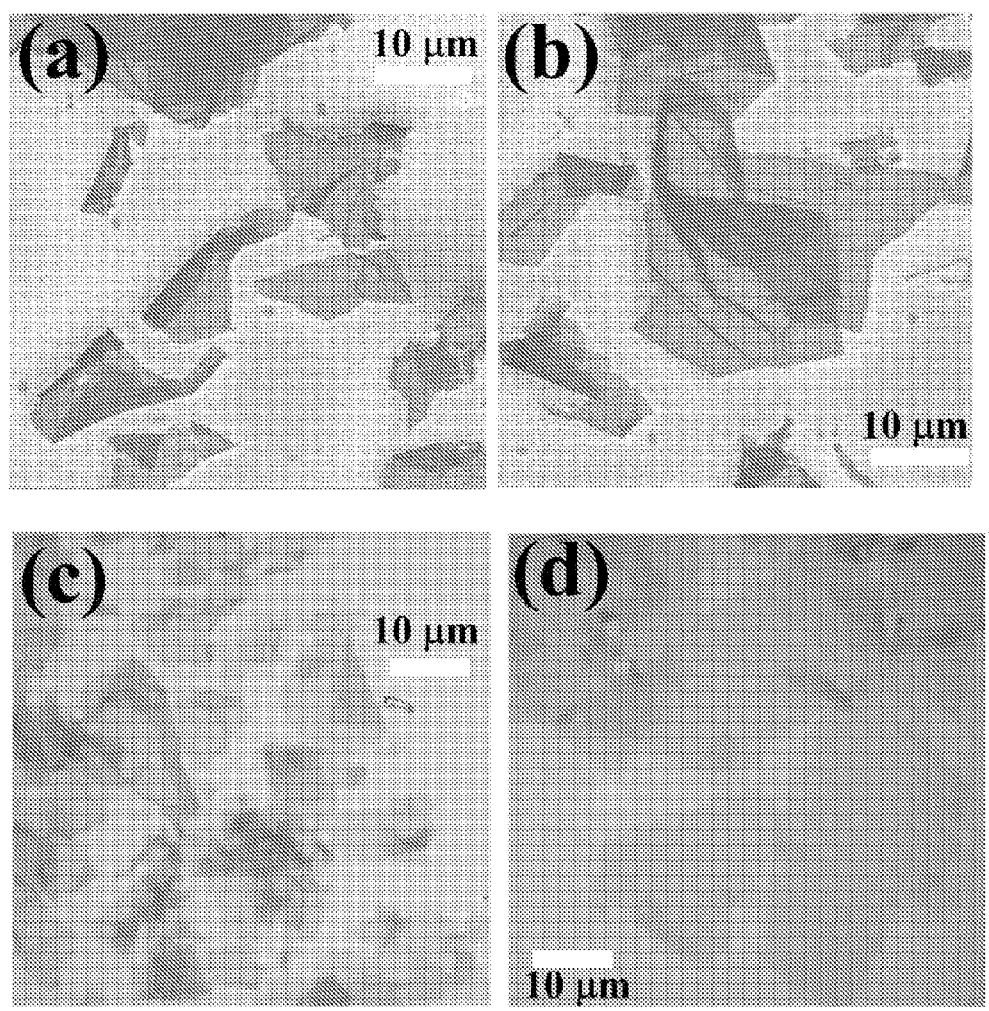

Figure S4
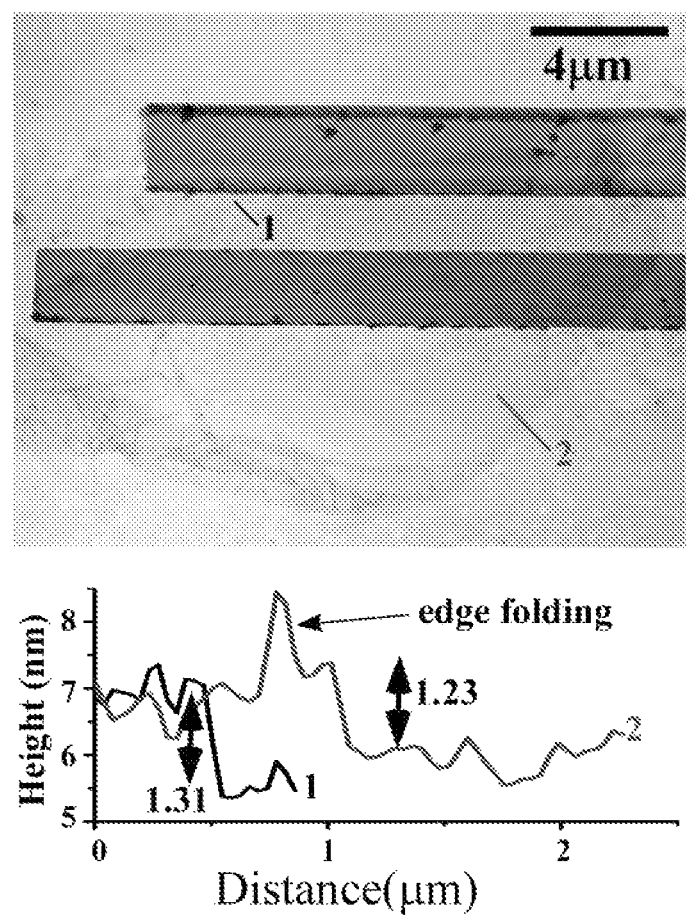

HIGH YIELD PREPARATION OF MACROSCOPIC GRAPHENE OXIDE MEMBRANES

CROSS-REFERENCE TO RELATED APPLICATIONS

This application is the National Stage of International Application No. PCT/US2009/066685, filed Dec. 4, 2009, which claims the benefit of U.S. Provisional Application No. 61/140,555, filed Dec. 23, 2008, the disclosures of which are incorporated herein by reference in their entireties for all purposes.

STATEMENT OF GOVERNMENT RIGHTS

The government may have certain rights in this invention. The work underlying this invention was supported by the Joint Science and Technology Office (JSTO), Defense Threat Reduction Agency (DTRA), and Army Research Office grant W911NF-06-1-0462, and by the Nano/Bio Interface Center through the National Science Foundation grant DMR-0425780.

TECHNICAL FIELD

The present invention relates to graphene oxide membranes and to methods of synthesizing such materials.

BACKGROUND

Graphene is a single-atom thick, two-dimensional material that has attracted attention because of its unique electronic, mechanical, and thermal properties. Because of these characteristics, graphene is useful in a range of electronic devices—such as sensors—and there is a corresponding interest in methods of producing graphenic materials.

Existing methods of synthesizing graphene oxide ("GO") materials, however, yield only comparatively small (sub-micron) GO flakes that possess unremarkable electronic properties. Accordingly, there is a need in the field for methods of reliably synthesizing macroscopic GO membranes. The value of such methods would be further enhanced if the synthesis methods produced GO materials exhibiting enhanced electrical, mechanical, or thermal properties.

SUMMARY

In meeting the challenges described above, the present invention first provides methods of synthesizing a graphene oxide membrane, such methods comprising exposing graphite to microwave radiation so as to exfoliate at least a portion of the graphite into a layered structure; and oxidizing the layered structure so as to give rise to a graphene oxide membrane having an upper surface and a lower surface.

Also provided are membranes, such membranes comprising a graphene oxide membrane having at least an upper surface and a lower surface, the upper surface, the lower surface, or both comprising a surface area of up to about 2500 $\mu m^2$.

Further disclosed are sensor devices, said devices comprising a reduced graphene oxide membrane characterized as having an electrical conductivity in the range of from about 200 S/m to about 400 S/m; a biomolecule in electrical connection with the graphene oxide membrane; and a detector in electrical communication with the graphene oxide membrane, wherein the interaction between a biomolecule and its environment changes an electrical characteristic of the detector, the change being capable of being transmitted along at least a portion of the graphene oxide membrane to the detector.

Additionally provided are methods of detecting an analyte, said methods comprising providing a sensor device comprising a graphene oxide membrane having an electrical conductivity in the range of from about 200 S/m to about 400 S/m and a biomolecule in electrical connection with the graphene oxide membrane, the biomolecule being capable of binding to an analyte, wherein the binding of the analyte gives rise to an electrical change within the sensor device; exposing the biomolecule to the analyte to give rise to the analyte binding to the biomolecule; and monitoring a change in the electrical conductivity of the graphene oxide membrane effectuated by the binding of the analyte to the biomolecule.

Also disclosed are composite materials, said materials comprising a graphene oxide membrane having at least an upper surface and a lower surface, the upper surface, the lower surface, or both comprising a surface area of up to about 2500 $\mu m^2$, the graphene oxide membrane being incorporated into a polymeric material by way of one or more bonds to a repeat unit of the polymer.

Further provided are membranes, comprising a graphene oxide membrane, the membrane having an electrical conductivity of from about 200 to about 500 S/m.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings.

Figure 1:
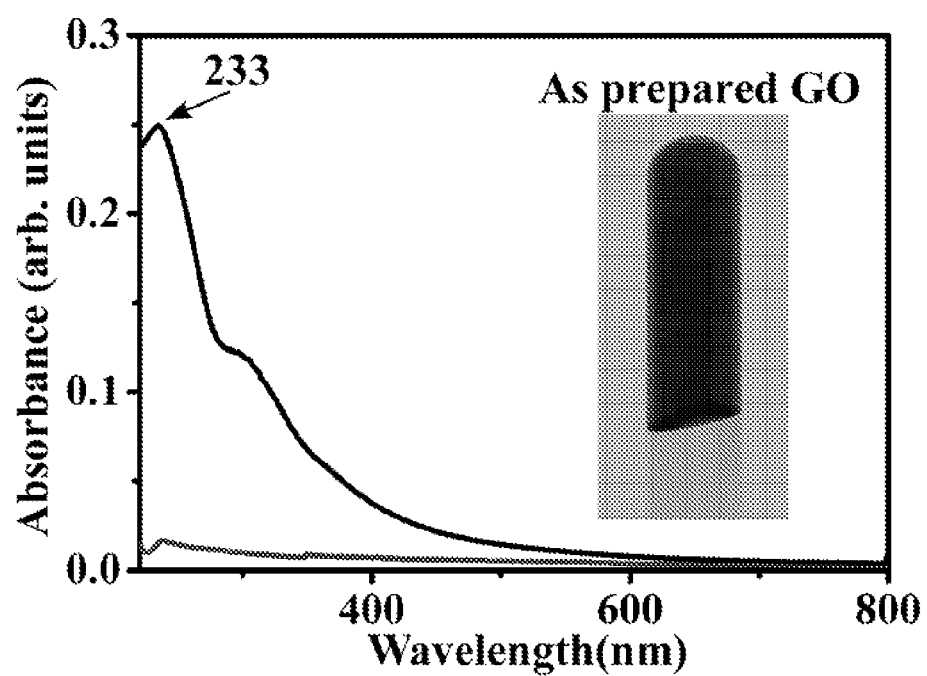
FIG. 1 depicts UV-vis absorption spectra of aqueous GO solution before and after filtration (pore size 0.45 $\mu m$), inset: photograph of the viscous, 0.3% (w/w) GO solution in an inverted test tube.

FIG. S1 depicts (a & b) Pictures and SEM image of graphite samples before and after microwave expansion, (c) Zoomed region in (b);

FIG. S2 depicts (a & b) X-ray diffraction pattern of graphene oxide membranes and their microwave-assisted expanded graphite;

FIG. S3 depicts SEM (a & b) and optical (c & d) image of graphene oxide membranes on $SiO_2$/Si substrate; and FIG. S4 depicts an AFM image of a typical graphene oxide Field effect transistor.

DETAILED DESCRIPTION OF ILLUSTRATIVE EMBODIMENTS

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

First provided are methods of synthesizing graphene oxide membranes. These methods entail exposing graphite to microwave radiation so as to expand/exfoliate at least a portion of the graphite into a layered structure, and then oxidizing the layered structure so as to give rise to a graphene oxide membrane having an upper surface and a lower surface.

The disclosed methods are suitably performed on graphite starting materials that comprise one or more acids intercalated within. Expandable graphites—such as Grafgard 160-50N (www.graftech.com)—that include acids such as sulfuric acid, nitric acid, and acetic acid are considered suitable. Other acids may be used to intercalate within such graphite materials; suitable acids will be readily identified by those of skill in the art without undue experimentation.

Suitable graphite materials, like the aforementioned Grafgard, are easily obtained. The materials are typically in the form of layered flakes or particles. Expandable graphite may also be molded or formed into various shapes as needed to meet the user's needs.

The microwave radiation used in the claimed methods is suitably of a frequency of between about 1 GHz and about 3 GHz, although higher frequencies of radiation may be used. As is known in the art, commercially-available microwave ovens—such as those used in homes—supply microwave radiation at a frequency of about 2.45 GHz, which frequency is considered suitable for these disclosed methods. The optimal power of the microwave radiation being applied will be easily determined by those of skill in the art, and can vary from 0.01 GHz to about 10 or even 50 GHz. Radiation in the range of from about 1 GHz to about 10 GHz, or even from about 2 GHz to about 7 GHz is considered especially suitable. Microwave ovens suitable for home use are known to provide microwave radiation having a power in the ranges of tens, hundreds or even thousands of watts, which power levels are suitable for the claimed methods.

As is described elsewhere herein, the expandable graphite may be purged with a neutral gas—such as nitrogen—before application of the microwave radiation. Other species, including inert or even nobel gases, are considered suitable purging agents. Without being bound to any particular theory, it is believed that this removes impurities or other species that may adversely participate in the expansion process, and thus results in an expanded graphite product that is of greater purity and regularity of structure than that produced by other processes known in the art. This theory is confirmed—as discussed in the Examples section below—by the fact that GO membranes produced according to the claimed methods exhibit improved electrical properties as compared to GO membranes produced by other, existing methods. Thus, it is believed that application of the microwave radiation effects rapid gasification of the intercalated species, and fewer defects are then caused by oxidation from the intercalated compounds or from oxygen that is otherwise absorbed.

Under microwave radiation, the expandable graphite may expand by 10, 50, 100, 200, or even—in some cases—up to 500 times its original volume, to form a layered structure. Once the graphite is expanded by application of microwave energy, the material may be separated into flakes. Such flakes may suitably have the same lateral dimension (e.g., width, diameter) as the graphite starting material, but may also be about 100 times thinner than the graphite starting material. Graphite that does not fully expand under exposure to microwave radiation may be picked out or separated from the expanded graphite.

The microwave radiation is suitably applied to the graphite for from between about 0.1 and about 5 or even about 10 seconds. Application of the radiation for only 2 seconds has been shown effective, as described in the Examples section elsewhere herein. The optimal combination of microwave frequency, power, and time-of-application will be easily determined by those of skill in the art, and may be dictated by the particular characteristics of the expandable graphite starting materials used.

Once the graphite is expanded, graphene oxide is suitably formed by oxidizing the expanded, layered material. Such oxidation processes will be known to those in the art, and may include the known Hummers method, the known Staudenmeier method, and other oxidation methods in the field. Oxidizing is suitably accomplished—as described in the Examples section further herein—by exposing the expanded graphite to sulfuric acid, nitric acid, potassium chlorate, potassium permanganate, potassium persulfate, hydrogen peroxide, phosphorus pentoxide, sodium chloride oxide, or other oxidizers, singly or in combination. The oxidation is suitably performed with care, as certain oxidizers are hazardous and should be handled with caution.

Oxidation may, in some embodiments, be performed in a medium that is substantially water-free, although such a medium is not critical to the success of the disclosed methods. The result of the described synthesis methods is a comparatively large grapheme oxide membrane, which membranes can be from between 10 to 3000 $\mu m^2$ in size, or from about 100 to about 1000 $\mu m^2$ in size, or even from about 500 to about 750 $\mu m^2$ in size. The membranes may also have a thickness of from about 0.5 to about 2.0 nm, or even about 0.6 to about 1 nm, or even 0.80 or about 0.83 nm.

Once the expanded graphite is oxidized to form the graphene oxide membranes, the resulting membranes is suitably centrifuged and washed, e.g., with deionized ("DI") water. In some embodiments, the membrane is washed until a stabilized pH value of about 5, 5.5, 6, or 6.5 is reached. A change in viscosity is observed with this process, which indicates that exfoliation has occurred.

Ultrasonication or other physical force applied to the membranes to separate them is not necessary. In some embodiments, however, ultrasonication may be used to separate the membranes or, in some cases, to modify the size of the membranes by imposing mechanical stress on the membranes.

Figure 3:
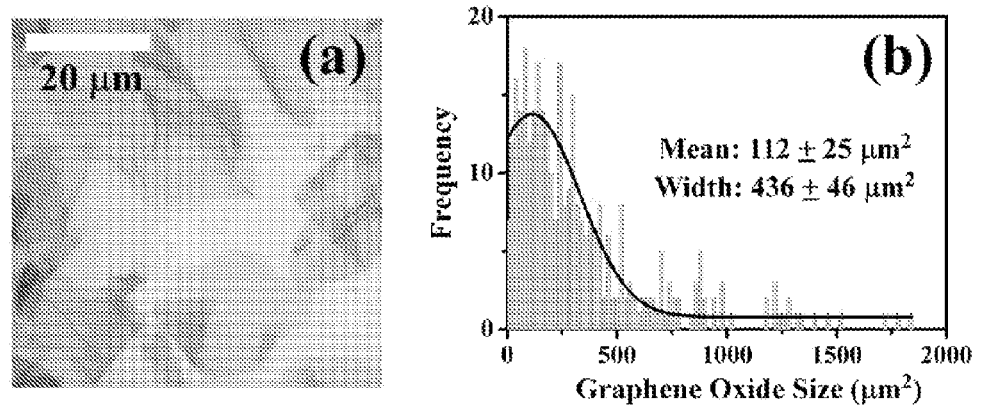
FIG. 3 depicts (a) Optical micrograph of reduced GO on $SiO_2$/Si, (b) Size distribution of GO membranes, solid curve is a Gaussian fit.

A user of grapheme oxide membranes made by the disclosed methods may, in some cases, desire an increased visual contrast between the membrane and the visual background. To achieve such a contrast, the membranes may be exposed to hydrazine, which results in a grapheme oxide membrane that is easily visualized without resort to inefficient and potentially destructive methods, such as atomic force microscopy (AFM) or scanning electron microscopy (SEM). Membranes exposed to hydrazine, on the other hand, are easily imaged on a substrate of 300 nm $SiO_2$/Si, as shown in FIG. 3. The increased optical contrast provided by this method enables the user to locate a membrane and locate one or more regions within the membrane for fabrication of GO-based devices.

Along with their comparatively large size, the membranes produced by the disclosed methods also exhibit useful electrical properties. The membranes produced according to the claimed methods display particularly high conductivity values, which values can be from about 10, 50, 100 200, 400, or even up to about 500, about 1000, or even about 5000 S/m. In one embodiment (shown in FIG. 4 and also described in the Examples section elsewhere herein), a GO membrane exhibited a calculated conductivity of about 440 S/m, which is superior to the values of 5-200 S/m that have been previously reported. GO membranes made according to the claimed methods are also within the scope of the invention.

Also described are GO membranes. These membranes include a graphene oxide membrane having at least an upper surface and a lower surface, the upper surface, the lower surface, or both comprising a surface area of up to about 3000 $\mu m^2$. In exemplary membranes, the upper or lower surface of the membrane has a surface area in the range of from about 400 $\mu m^2$ to about 3000 $\mu m^2$, or from about 800 to about 2000 $\mu m^2$, or even about 1750 $\mu m^2$.

The membranes are also characterized by useful electrical properties, and suitably possess electrical conductivity values of from about 3 S/m to about 500 S/m, or from about 100 to about 450 S/m, or even about 400 S/m. Exiting graphene fabrication methods, by contrast, produce graphene with conductivity values of only about 5 S/m to about 200 S/m (Gilje et al., *Nano Lett.* 2007, 7, 3394; Gomez-Navarro et al., *Nano Lett.* 2007, 7, 3499). The membranes may also be divided into subunits or smaller pieces, as needed; techniques for doing such division will be known to those of skill in the art.

In some embodiments, the GO membranes have a surface area of less than about 2500 $\mu m^2$. In other embodiments, the GO membranes have an electrical conductivity value of at least about 300 S/m. In some embodiments, the conductivity is from about 200 to about 500 S/m. In these embodiments, the membranes are of a comparatively lower surface area form, such as a strip, rectangle, curve, or other configuration.

Owing to their comparatively large surface areas, the disclosed membranes also suitably comprise a diameter/thickness ratio in the range of from about 100 to about 40,000, or from about 500 to about 10,000, or from about 1000 to about 3000. As described elsewhere herein, the membranes are based upon layers derived from expanding graphite, and these layers may have a thickness that, in some embodiments, is only 1/100 or less than the thickness of the graphite starting material.

The present invention also provides sensor devices. Such devices suitably include a reduced graphene oxide membrane characterized as having an electrical conductivity in the range of from about 150 S/m to about 500 S/m, or from about 200 to about 400 S/m, a biomolecule in electrical connection with the graphene oxide membrane; and a detector in electrical communication with the graphene oxide membrane, wherein the interaction between a biomolecule and its environment effects a change in an electrical characteristic of the detector, the change being capable of being transmitted along at least a portion of the graphene oxide membrane to the detector.

The graphene oxide membranes used in these sensors are suitably the graphene membranes described elsewhere herein. The membranes may be of varying size, and, in some embodiments, may be larger than 2000 $\mu m^2$, or even larger than 2500 $\mu m^2$ or 3500 $\mu m^2$ in surface area.

In some embodiments, the GO membranes include one or more functional groups (e.g., —COOH, —OH). Depending on the functional group, such groups may be added before or after the oxidation step. The groups may be useful in linking biomolecules or other species to the GO membrane, and the chemistry used to perform such linkage will be known to those of skill in the art.

The sensorts suitably include one or more biomolecules is bound to the membrane. The biomolecule is suitably on the basis of an ability to bind to an analyte of interest. For example, if the user desires to detect the presence of a particular antigen might bind to the membrane an antibody known to be complementary to that antigen. Ligands, receptors, oligonucleotides, and the like are all considered suitable biomolecules.

Biomolecules can be nucleic acids, proteins, antibodies, antigens, and the like. Ligands and receptors may also be used. While biomolecules are useful because of their ability to bind specifically to a particular analyte, it is to be understood that the disclosed detectors are not limited to the use of only biomolecules to bind or assay for the presence of a particular analyte. Other species—such as synthetically-constructed oligomers, polymers, and the like—may also be used in place of or with biomolecules to detect the presence of analytes in a particular medium.

Single-stranded DNA (known as "ssDNA") is a biomolecule of particular utility. Because the sequence of the ssDNA is easily modified, ssDNA can be tailored to a variety of configurations. Because it is known that particular sequences of ssDNA are specifically responsive to various analytes, one or more sequences of ssDNA can be bound or otherwise disposed on a GO membrane to allow for parallel detection of multiple analytes. Because ssDNA is easily synthesized, those of skill will encounter little difficulty in synthesizing ssDNA fragments of the desired sequence.

As discussed, biomolecules may be chosen based on their ability to bind to a specific target. In some embodiments, the biomolecule may be chosen based on its ability to bind to a class of targets. For example, a user may employ a biomolecule that binds to the entire family of *Streptococcus* bacteria, not just to a single member of that family. Biomolecules may be bound to the GO membranes by various known methods; the user of skill in the field will encounter little difficulty in selecting a binding method by which to attach a biomolecule to the GO membrane. In some embodiments, the bond or linkage between the biomolecule and the GO membrane is electrically conductive; in such embodiments, interactions between a biomolecule and its intended target or targets will effect a change in some electrical characteristic of the sensor assembly that is detectable by way of an electrical connection to the GO membrane. Thus, the detector is preferably constructed such that it is capable of detecting a signal evolved from the binding of the biomolecule to a target.

In some embodiments, the detector may be used to detect the release or un-binding of a target from a biomolecule located on the sensor. In other embodiments, the detector may include multiple biomolecules. In these embodiments, the biomolecules are selected so as to permit parallel detection of analytes. For example, a sensor may be constructed with two different biomolecules, each of which exhibits a different electronic signature when exposed to the analyte to which the biomolecule is complementary. By detecting the presence of these differing electronic signatures, the binding of two—or more—analytes can be detected in parallel. Biomolecules, analytes, or both, may also be labeled with fluorescent, magnetic, or radioactive labels so as to enable the user to detect binding or lack thereof.

The disclosed sensors are suitably in electrical connection with a computer or other analysis device. The analysis device suitably receives one or more signals from the detector and displays, records, or otherwise processes the signals to determine the presence of a particular analyte. The sensors and associated equipment may be calibrated by detecting an analyte known to be present and then comparing that signal to the signal evolved when the sensors are contacted with a medium containing an unknown analyte.

The detectors are suitably exposed to the analyte in a fluid medium. The medium may be flowed over the detector, in other cases, the detector may be immersed in the medium. Electrical signals related to the binding of analytes to the biomolecules on the detectors may be monitored in real time, or recorded for later analysis. The analytes may be present in a solid or vaporous medium, in some embodiments.

The electrical signals evolved from the binding of an analyte to the biomolecule on the detector may be a change in current, voltage, resistance, capacitance, and the like. Binding of the analyte to the biomolecule can effect a change in two or more electrical characteristics.

In addition to their use as sensors, the disclosed materials can be used in other electronic devices to take advantage of their favorable electronic properties. As one example, the membranes can be used in transistors and other devices.

The GO membranes described herein are also suitable for use in composite materials. Such materials suitably include a GO membrane as described elsewhere herein, with the membrane being incorporated into a polymeric material by way of one or more bonds to a repeat unit of the polymer.

Suitable polymers will be known to those of skill in the art. A non-limiting listing of such materials includes polyolefins, polyamides, polycarbonate, polyesters, and the like. Suitably polyolefins include polyethylene, polypropylene, polybutene, cyclic polyolefin, or any combination thereof. The polymer may be a homopolymer, a copolymer, a block copolymer, a branched polymer, a graft polymer, a star polymer, a dendrimer, or combinations thereof.

The GO membranes, as described in the Examples section below, are also known to be water-soluble. This was shown by washing the membranes evolved from oxidizing the microwave-expanded graphite in water and observing that the GO membranes suspended in the water (FIG. 1). That the GO membranes are water-soluble makes them particularly suitable for incorporation into polymeric materials. By contrast, carbon nanotubes are known to stick together and aggregate, which characteristic makes such nanotubes unsuitable for certain applications and dispersions.

Non-Limiting Examples and Exemplary Embodiments

Graphene is a single-atom thick, two-dimensional material that has attracted great attention because of its remarkable electronic, mechanical, and thermal properties. This has led to renewed interest in methods to chemically functionalize and exfoliate graphite in bulk. However, previously reported methods resulted in the production of very small (sub-micrometer) flakes of graphene oxide (GO) with only moderate quality electronic transport properties after chemical reduction. The small flake size is a major obstacle that hinders fundamental studies and limits applications of this material. A practical method appropriate for large-scale production of single layer GO with large size and high quality electric properties is an important step towards the rapid and large-scale fabrication of graphene-based devices, and it will facilitate applications in the areas of electronics, molecular sensors and composite materials.

Described here is a GO synthesis method that involves pre-exfoliation of the graphite by microwave heating. With this approach are produced gram quantities of large single layer GO membranes, up to 2000 $\mu m^2$ in size, with a yield exceeding 90%. When the large membranes are deposited on appropriate $SiO_2$/Si wafer and chemically reduced, they can be visualized optically, so electronic devices may be efficiently fabricated. Electronic transport measurement on such samples indicates that their conductivity is significantly higher than previously reported single layer GO devices.

In a synthesis according to the disclosed invention, microwave-assisted heating is used to expand the graphite into thinner layer structure. Specifically, a small amount of expandable graphite (e.g., Grafguard 160-50N), is sealed in a glass vial, purged with ultra high purity nitrogen for 2 hours, and then heated in a microwave oven for less than 2 seconds. The high polarizabilty of graphene layers cause them to heat rapidly under microwave irradiation. The intercalated species gasify rapidly, and, without being bound to any particular theory, fewer point defects are generated by oxidation from intercalated compounds and robustly absorbed oxygen compared to conventional thermal expansion. The graphite expands to ~200 times its original volume, (see FIG. S1), and is separated into flakes whose thickness is 100 times less than the starting material, but whose lateral dimension is effectively unchanged relative to the starting material.

Using such pre-expanded few layer graphite as a starting material, GO is then prepared using the Hummers method, although other methods of oxidation known in the art are also suitable. Because of the pre-expansion process, high viscosity saturated solutions are produced using only 0.5% (w/w) of microwave expanded graphite, in contrast to conventional methods, where ~50 times more graphite is required. The product after oxidation is centrifuged and washed with DI water extensively until the pH stabilizes at ~5.5. No ultrasonication is used, which is an advantage over existing methods that do require a sonication step, which sonication can disrupt, fracture, or otherwise damage the graphenic materials and can break flakes down into smaller, less-useful fragments. During the water wash, a significant viscosity change was observed, indicating that exfoliation continues in this process. The addition of salt to the resulting solution induces aggregation of the membranes, suggesting that they are charge-stabilized. Only minute amounts (<1%) of un-exfoliated graphite are observed. A single sharp peak is observed in the X-ray diffraction from a filter cake (FIG. S2), corresponding to GO layer-layer distance of ~0.94 nm, as expected for complete exfoliation.

FIG. 1 illustrates the UV-vis absorption spectrum of a 0.003% (w/w) GO solution, compared with the absorption of the filtrate through 0.45 µm pore size filter. Two main features are seen: (1) a peak at 233 nm, which is due to $\pi \rightarrow \pi^*$ of C=C, and (2) a shoulder at ~290-300 nm, corresponding to $\pi \rightarrow \pi^*$ transition of C=O bond. The absorbance at 233 nm of the filtrate is less than 10% of that original solution, corroborating visual observation that the filtrate is clear and colorless. These data indicate that the majority of GO flakes are significantly larger than 1 µm in size, consistent with Atomic Force Microscopy (AFM; see below). The material is soluble in many solvents, e.g., acetone, methanol, ethanol, dimethylformamide, tetrahydrofuran, N-methyl-2-pyrrolidinone, and dimethyl sulfoxide.

Figure 2:
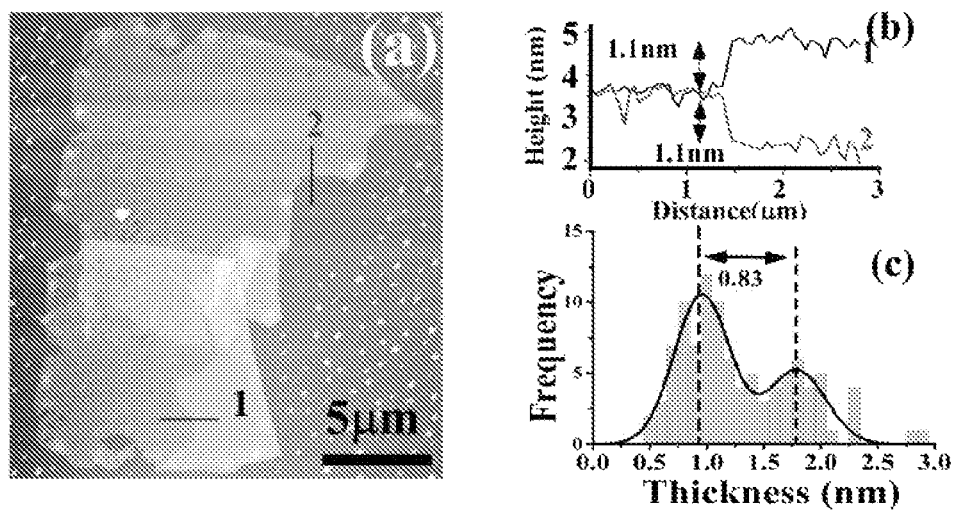
FIG. 2 depicts (a) AFM image of a graphene oxide membrane on a $SiO_2$/Si substrate, (b) Height profile along the lines shown in (a), (c) Histogram of sheet thickness.

FIG. 2 is a typical tapping mode AFM image of a GO membrane deposited on $SiO_2$/Si substrate by spin-coating. The areas of the upper and lower are approximately 160 and 110 $\mu m^2$, the equivalent of lateral diameters of 14 and 11 $\mu m$, respectively. The membrane height is ~1 nm (FIG. 2*b*). A GO membrane thickness histogram compiled from multiple AFM images (FIG. 2*c*) reveals peaks centered at 0.96 and 1.79 nm. The first peak is assigned to the average height of single layer GO on $SiO_2$, consistent with previous reports of 0.8-1.5 nm. The peak-to-peak difference of 0.83 nm is in the range of interlayer distances of 0.68-1.0 nm inferred from x-ray diffraction measurements of GO powder and very close to the 0.82 nm value obtained from a theoretical structure model of hydroxylated graphene. Residual un-exfoliated graphite is insignificant in this sample, since its presence would lead to peaks separated by 0.34 nm in FIG. 2*c*, and multiple peaks in the XRD pattern, which is not seen.

Another obstacle preventing fabrication of GO nano-scale devices is the difficulty of locating individual flakes without using inefficient and potentially destructive methods, such as AFM or scanning electron microscopy (SEM). GO membranes reduced by exposure to hydrazine are readily imaged on the surface of 300 nm $SiO_2$/Si. CAUTION: Hydrazine is extremely corrosive and should be handled with care. The significant optical contrast and the very large membrane size make it straightforward to locate membranes and to select a region that is optimized for fabrication of GO-based devices. FIG. 3(*b*) shows a size histogram of GO membranes observed using optical microscopy and HRSEM (see FIG. S3). The majority of the GO membranes are 2-3 orders of magnitude larger in area than those produced using previously reported methods.

The high-yield production of macroscopic GO membranes does not derive simply from the use of large starting graphite material, since sub-micrometer flakes are produced by recently reported methods even when large grain (400 $\mu m$) starting material is used. Microwave-assisted pre-expansion is critical to the process; without this step, very few large GO membranes are obtained. The microwave pre-expansion yields a fluffy material with graphite flakes that are 2-3 orders of magnitude thinner than the bulk (see FIG. S1). Without being bound to any single theory, this high yield of large single sheets may be due to the fact that stronger reaction conditions usually required for graphite exfoliation (e.g. ultrasonication) are not used in the present methods. Microwave pre-exfoliation of graphite enables faster, more uniform functionalization under milder conditions.

Figure 4:
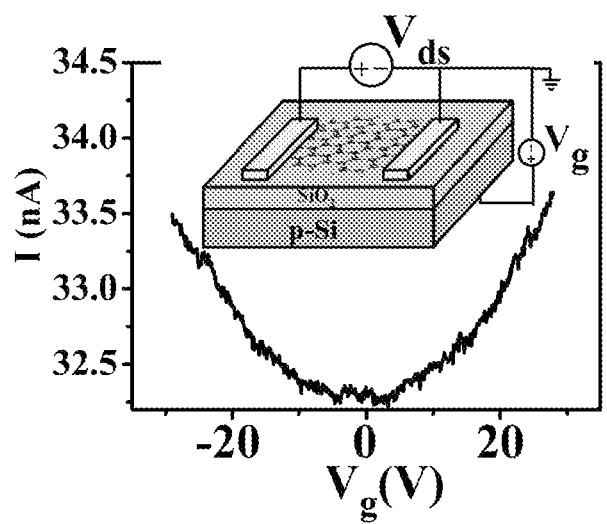
FIG. 4 depicts I-Vg characteristic of a reduced, single-layer graphene oxide (GO) sample ($V_{ds}$=10 mV), inset: schematic of GO field effect transistor.

Electron beam lithography and thin film evaporation were used to fabricate Au/Cr source and drain electrodes in a field effect transistor (FET) configuration, with the doped silicon substrate used as a back gate (see FIG. S4). Measurable drift was observed during the first few current-gate voltage (I-$V_g$) sweeps, after which the I-$V_g$ measurement stabilized. This may be attributed to unbinding of weakly bound oxidative groups in the presence of the gate electric field. FIG. 4 shows a typical, stabilized I-$V_g$ curve of a single-layer GO sample that was measured under ambient conditions (source-drain bias voltage $V_{ds}$=10 mV). The "V" shape of the I-$V_g$ curve indicates that the reduced GO shows ambipolar behavior, similar to that observed for single layer graphene. Taking into account the sample geometry (29 $\mu m$ length, 3 $\mu m$ source and drain separation, and assumed thickness of 0.83 nm), the conductivity of the GO membrane is 440 S/m (370 S/m if a layer thickness of 1 nm is assumed), significantly greater than previous reports of 5-200 S/m. This observation is consistent with the suggestion that the microwave pre-expansion step preserves the graphite layer structure and reduces the number of defects introduced during the chemical oxidation step.

In sum, provided is a high-yield synthetic protocol for single layer GO membranes, with sizes of several thousand square micrometers. GO membranes reduced in hydrazine can be located optically on $SiO_2$/Si substrates, enabling rapid fabrication of electronic devices. Electronic transport measurements indicate that the GO conductivity is significantly higher than previous reports. The ability to create solutions of such large membranes with high yield should enhance the utility of GO for electronic applications. In addition, the accessibility of dense, aqueous solutions of structures with an unprecedentally high diameter/thickness ratio (up to 40,000) will enable further experiments probing fundamental physics and chemistry in this unusual size regime.

Additional Details

Chemicals. Acid intercalated expandable graphite (Grafguard 160-50N, mean particle size: 350 $\mu m$, the graphite was intercalated with organic acid and sulfuric acid and nitric acid.) was kindly provided by Graftech Inc. Concentrated sulfuric acid ($H_2SO_4$), Potassium peroxodisulfate ($K_2S_2O_8$), Phosphorus (V) oxide ($P_2O_5$), Potassium permanganate ($KMnO_4$), hydrogen peroxide ($H_2O_2$), anhydrous hydrazine ($N_2H_4$) was purchased from Aldrich. All chemical were used as received unless otherwise stated.

Microwave assisted expansion of expandable graphite. A small amount of expandable graphite was sealed in a glass vial and purged with high purity nitrogen for 2 hours. The vial was then heated in a microwave oven (Panasonic, model NN-S547WA, 60 Hz) for less than 2 s. Graphite that had not expanded fully was carefully picked out.

Oxidation and exfoliation of expanded graphite. Graphene oxide (GO) was prepared according to the Hummers method, although other oxidation methods known in the art are suitable. $K_2S_2O_8$ (5 g) and $P_2O_5$ (5 g) were mixed with concentrated sulfuric acid (30 ml) at 90° C. Then 150 mg of microwave-expanded graphite was carefully added to the solution while stirring. The reaction was keep at 80° C. for 4.5 hours. On completion of the reaction, the mixture was added to excess de-ionized water, followed by filtration through a 0.2 micron Nylon Millipore filter and washing with excess water until the pH of the filtrate was close to neutral. The fluffy graphite oxide was dried in air at 60° C. for 3 hours. The dried sample was then added to concentrated sulfuric acid (100 ml) at 0° C. $KMnO_4$ (60 g) was then added slowly until dissolved. The reaction was kept at 35° C. for 2 hours. Again, the mixture was added to 1 L de-ionized water and stirred for 2 h. Then 50 ml of 30% $H_2O_2$ was added very slowly, and the mixture allowed to settle for 24 hours. Warning: this solution is very corrosive and must be treated with extreme caution; it reacts violently with organic material. The sediment was decanted and the remaining solution was then centrifuged and washed with a total of 1 L of 10% HCl solution three times, then centrifugated again and washed with 1 L of DI water 10 times. The final graphene oxide solution is then concentrated to ~230 ml, yielding a very viscous, brownish transparent solution with concentration 0.30% (w/w). Trace amounts of ions are then removed by dialysis against deionized water for 60 days, using tubing with a 12,000 MW cutoff (Fisher Scientific).

X-ray diffraction. A small amount of graphene oxide membrane solution was dried at room temperature under vacuum for 12 hours until no further weight loss was observed. The x-ray diffraction (XRD) of this material was performed on a Rigaku GiegerFlex D/Max-B X-ray diffractometer at 40 kV and 20 mA for monochromatized Cu Kα (λ=0.15416 nm) radiation. For graphene oxide the film, an INEL CPS120 powder diffractometer with position-sensitive detector covering 120 degree range of 2θ at 40 kV, 20 mA with Cu target (1.5416 angstroms) and graphite HOPG low resolution monochromator. The graphene oxide sample was rotated continuously during data accumulation to average out the effects of preferred orientation in the diffracting plane. Basal distances of (002) planes were calculated according to the Bragg equation.

Deposition of graphene membrane on $SiO_2$/Si substrate. Alignment markers were fabricated on the oxidized silicon substrate ($SiO_2$ thickness of 300 nm) using photolithography and thin film evaporation of 3 nm Chromium and Gold. 20 μl of sample solution was diluted with 2 ml of DI water. 100 μl of the diluted solution was spin-coated onto the substrate at 3000 r.p.m. for 1 minute. The GO/substrate and an open vial of 200 μl hydrazine was then sealed in large glass container and kept at 50° C. for 24 hours to reduce the graphene oxide.

Atomic Force Microscope (AFM). Tapping mode AFM was used to acquire the images under ambient conditions (Digital Instruments Multimode AFM).

High resolution Scanning Electron Microscope (HRSEM). SEM images were acquired with a JSM-7500F (JOEL), using a 2 kV accelerating voltage in gentle beam mode (bias voltage applied to the specimen stage).

Fabrication of GO transistor using electron beam lithography. Source and drain electrodes were patterned by electron beam lithography using polymethylmethacrylate PMMA as the e-beam resist. Single layer graphene oxide membranes on an oxidized silicon substrate (300 nm $SiO_2$ thickness with pre-fabricated alignment markers; see above) were first identified and located by optical microscopy. Then, 100 μl of 5% PMMA (relative molecular mass, 495K) chlorobenzene solution was applied to the substrate at 3000 rpm, followed by baking at 180° C. for 2 minutes. Based on spin curves provided by the manufacturer (Microchem Corp., www.microchem.com), the PMMA thickness is about 300 nm. Electron-beam patterning was done using a JOEL SEM 6400 operated at 30 kV with a Raith Elphy Plus controller, with an exposure dosage 500 μA/cm$^2$. The exposed PMMA was developed with a methyl isobutyl ketone (MIBK) and isopropyl alcohol (1:3) solution. Chromium (3 nm from R.D. Mathis company) and Gold (50 nm) were then deposited onto the substrate in a thermal evaporator with a cryopump producing a base pressure of $10^{-7}$ Torr. The deposited films were then lifted off in acetone bath for 12 h at 70° C. and rinsed extensively with isopropyl alcohol.

Electronic transport measurement. The bulk of the heavily doped p++ (conducting) silicon substrate was used as the gate electrode, with contact made to the chip with silver paint. Source, drain and gate electrodes were contacted using three individual probes in a homemade, small-signal probe station, which is controlled using Labview. A DAC card (National Instruments) installed in a PC (Dell) was used to output source-drain voltage, and a Keithley 6517A current meter was used to read the source-drain current and to output the gate voltage.

What is claimed:

1. A method of synthesizing a graphene oxide membrane, comprising:
    exposing graphite to microwave radiation so as to exfoliate at least a portion of the graphite into a layered structure; and
    oxidizing the layered structure so as to give rise to a graphene oxide membrane having an upper surface and a lower surface;
    wherein the oxidizing is performed after exposure to microwave radiation.

2. The method of claim 1, wherein the graphite comprises an acid intercalated therein.

3. The method of claim 2, wherein the acid comprises an organic acid, sulfuric acid, nitric acid, or any combination thereof.

4. The method of claim 1, wherein the microwave radiation comprises a frequency of between about 1 GHz and about 3 GHz.

5. The method of claim 1, wherein the microwave radiation is applied for about 0.1 to about 5 seconds.

6. The method of claim 1, wherein the oxidizing is accomplished by exposure to sulfuric acid, nitric acid, potassium chlorate, potassium permanganate, potassium persulfate, hydrogen peroxide, phosphorus pentoxide, sodium chloride oxide, or any combination thereof.

7. The method of claim 6, wherein the exposure takes place in a medium that is substantially water-free.

8. The method of claim 1, further comprising the step of exposing the graphene oxide membrane to hydrazine.

9. The method of claim 1, wherein the volume of the layered structure is at least about 200 times the volume of the graphite.

10. The method of claim 1, wherein the upper surface of the membrane, the lower surface of the membrane, or both, comprises a surface area in the range of from about 400 μm$^2$ to about 3000 μm$^2$.

11. The method of claim 1, wherein the graphene oxide membrane has an electrical conductivity of about 400 S/m.

12. The method of claim 1, further comprising centrifuging and washing after the oxidizing step, wherein the method of synthesizing is free of ultrasonication or application of other physical force to separate the layered structure.

* * * * *

UNITED STATES PATENT AND TRADEMARK OFFICE
CERTIFICATE OF CORRECTION

PATENT NO. : 8,821,745 B2  
APPLICATION NO. : 13/141402  
DATED : September 2, 2014  
INVENTOR(S) : Zhengtang Luo et al.

It is certified that error appears in the above-identified patent and that said Letters Patent is hereby corrected as shown below:

In the Specification

Column 1,
After "STATEMENT OF GOVERNMENT RIGHTS", remove the paragraph at Lines 17-23 in its entirety and replace with the following – This invention was made with government support under grant numbers W911NF-06-1-0462 awarded by the U.S. Army Research Laboratory Army Research Office and DMR0425780 awarded by the National Science Foundation. The government has certain rights in the invention.

Signed and Sealed this
Fourteenth Day of April, 2015

Michelle K. Lee
*Director of the United States Patent and Trademark Office*